United States Patent [19]

Phan et al.

[11] Patent Number: 5,427,696
[45] Date of Patent: Jun. 27, 1995

[54] BIODEGRADABLE CHEMICAL SOFTENING COMPOSITION USEFUL IN FIBROUS CELLULOSIC MATERIALS

[75] Inventors: Dean V. Phan, West Chester; Paul D. Trokhan, Hamilton; Toan Trinh, Maineville, all of Ohio

[73] Assignee: The Procter & Gamble Company, Cincinnati, Ohio

[21] Appl. No.: 4,333

[22] Filed: Jan. 14, 1993

Related U.S. Application Data

[63] Continuation-in-part of Ser. No. 865,597, Apr. 9, 1992, Pat. No. 5,264,082, and a continuation-in-part of Ser. No. 865,596, Apr. 9, 1992, Pat. No. 5,262,007.

[51] Int. Cl.$^6$ .......................................... D21H 21/24
[52] U.S. Cl. ...................... 252/8.6; 252/8.8; 252/8.9; 162/158
[58] Field of Search ............ 162/158; 252/8.6–8.9

[56] References Cited

U.S. PATENT DOCUMENTS

| | | | |
|---|---|---|---|
| 2,683,087 | 7/1954 | Reynolds, Jr. ................ | 162/158 |
| 2,683,088 | 7/1954 | Reynolds, Jr. ................ | 162/158 |
| 3,301,746 | 1/1967 | Sanford et al. ............... | 162/113 |
| 3,554,863 | 1/1971 | Hervey et al. ................ | 162/158 |
| 3,755,220 | 8/1973 | Freimark et al. ............. | 260/17.3 |
| 3,817,827 | 6/1974 | Benz .............................. | 162/113 |
| 3,844,880 | 10/1974 | Meisel, Jr. et al. ........... | 162/169 |
| 3,974,025 | 8/1976 | Ayers ........................... | 162/113 |
| 3,994,771 | 11/1976 | Morgan, Jr. et al. .......... | 162/113 |
| 4,144,122 | 3/1979 | Emanuelsson et al. ....... | 162/158 |
| 4,158,594 | 6/1979 | Becker et al. ................. | 162/112 |
| 4,191,609 | 3/1980 | Trokhan ........................ | 162/113 |
| 4,300,981 | 11/1981 | Carstens ....................... | 162/109 |
| 4,303,471 | 12/1981 | Laursen ........................ | 162/158 |
| 4,351,699 | 9/1982 | Osborn, III ................... | 162/112 |
| 4,377,543 | 3/1983 | Strohbeen et al. ........... | 264/120 |
| 4,425,186 | 1/1984 | May et al. .................... | 162/158 |
| 4,432,833 | 2/1984 | Breese .......................... | 162/158 |
| 4,441,962 | 4/1984 | Osborn, III ................... | 162/111 |
| 4,447,294 | 5/1984 | Osborn, III ................... | 162/158 |
| 4,529,480 | 7/1985 | Trokhan ....................... | 162/109 |

(List continued on next page.)

FOREIGN PATENT DOCUMENTS 3608093 9/1987 Germany .
61308312 7/1988 Japan .

OTHER PUBLICATIONS

"Applications of Armak Quaternary Ammonium Salts", Bulletin 76-17, Armak Co., (1977). no month available.

*Primary Examiner*—Paul Lieberman
*Assistant Examiner*—Michael P. Tierney
*Attorney, Agent, or Firm*—Bart S. Hersko; E. Kelly Linman; Jacobus C. Rasser

[57] ABSTRACT

Biodegradable chemical softening compositions are provided comprising a mixture of a quaternized ester-amine compound and a polyhydroxy compound. Preferred biodegradable quaternized ester-amine compounds include diester dialkyl dimethyl ammonium salts such as diester ditallow dimethyl ammonium chloride, diester di(touch hydrogenated)tallow dimethyl ammonium chloride and diester di(hydrogenated)tallow dimethyl ammonium chloride. Preferred polyhydroxy compounds are selected from the group consisting of glycerol, and polyethylene glycols and polypropylene glycols having a weight average molecular weight from about 200 to 4000.

The biodegradable chemical softening compositions are prepared by first mixing the quaternized ester-amine compound into the polyhydroxy compound at a specific temperature range wherein the polyhydroxy compound is miscible with the quaternized ester-amine compound and then diluting the mixture with a liquid carrier at a specific pH and temperature range to form an aqueous vesicle dispersion suitable for treating fibrous cellulosic material. The biodegradable chemical softening compositions disclosed herein are primarily intended for softening disposable paper products such as tissues and towels. However, the biodegradable chemical softening compositions can also be used to soften fibrous cellulosic materials in textile form.

32 Claims, 6 Drawing Sheets

U.S. PATENT DOCUMENTS

| | | | |
|---|---|---|---|
| 4,637,859 | 1/1987 | Trokhan | 162/109 |
| 4,643,919 | 2/1987 | Fu | 427/393.1 |
| 4,767,547 | 8/1988 | Straathof et al. | 252/8.8 |
| 4,789,491 | 12/1988 | Chang et al. | 252/8.75 |
| 4,795,530 | 1/1989 | Soerens et al. | 162/111 |
| 4,853,086 | 8/1989 | Graef | 162/157.6 |
| 4,885,102 | 12/1989 | Yamamura et al. | 252/8.8 |
| 4,937,008 | 6/1990 | Yamamura et al. | 252/8.8 |
| 4,940,513 | 7/1990 | Spendel | 162/112 |
| 4,959,125 | 9/1990 | Spendel | 162/158 |
| 4,981,557 | 1/1991 | Bjorkquist | 162/168.2 |
| 5,023,003 | 6/1991 | Yamamura et al. | 252/8.8 |
| 5,066,414 | 11/1991 | Chang | 252/8.8 |
| 5,133,885 | 7/1992 | Contor et al. | 252/8.6 |
| 5,154,838 | 10/1992 | Yamamura et al. | 252/8.6 |
| 5,217,576 | 6/1993 | Van Phan | 162/158 |
| 5,223,096 | 6/1993 | Phan et al. | 162/158 |
| 5,223,096 | 6/1993 | Phan et al. | 162/158 |
| 5,240,562 | 8/1993 | Phan et al. | 162/158 |
| 5,262,007 | 11/1993 | Phan et al. | 162/158 |
| 5,264,082 | 11/1993 | Phan et al. | 162/158 |

BIODEGRADABLE CHEMICAL SOFTENING COMPOSITION USEFUL IN FIBROUS CELLULOSIC MATERIALS

This is a continuation-in-part of application Ser. No. 07/865,597, filed Apr. 9, 1992, now U.S. Pat. No. 5,264,082, and application Ser. No. 07/865,596, filed Apr. 9, 1992, now U.S. Pat. No. 5,262,007.

FIELD OF THE INVENTION

This invention relates to a biodegradable chemical softener composition. More particularly, it relates to a biodegradable chemical softener composition useful for treating fibrous cellulose materials, such as tissue paper webs. The treated tissue webs can be used to make soft, absorbent paper products such as toweling, napkin, facial tissue, and toilet tissue products. The biodegradable chemical softening compositions described herein can also be used to soften cellulose materials in textile form.

BACKGROUND OF THE INVENTION

Paper webs or sheets, sometimes called tissue or paper tissue webs or sheets, find extensive use in modern society. Such items as paper towels, napkins, facial and toilet tissues are staple items of commerce. It has long been recognized that three important physical attributes of these products are their softness; their absorbency, particularly their absorbency for aqueous systems; and their strength, particularly their strength when wet. Research and development efforts have been directed to the improvement of each of these attributes without seriously affecting the others as well as to the improvement of two or three attributes simultaneously.

Softness is the tactile sensation perceived by the consumer as he/she holds a particular product, rubs it across his/her skin, or crumples it within his/her hand. This tactile sensation is a combination of several physical properties. One of the more important physical properties related to softness is generally considered by those skilled in the art to be the stiffness of the paper web from which the product is made. Stiffness, in turn, is usually considered to be directly dependent on the dry tensile strength of the web and the stiffness of the fibers which make up the web.

Strength is the ability of the product, and its constituent webs, to maintain physical integrity and to resist tearing, bursting, and shredding under use conditions, particularly when wet.

Absorbency is the measure of the ability of a product, and its constituent webs, to absorb quantities of liquid, particularly aqueous solutions or dispersions. Overall absorbency as perceived by the human consumer is generally considered to be a combination of the total quantity of liquid a given mass of tissue paper will absorb at saturation as well as the rate at which the mass absorbs the liquid.

The use of wet strength resins to enhance the strength of a paper web is widely known. For example, Westfelt described a number of such materials and discussed their chemistry in Cellulose Chemistry and Technology, Volume 13, at pages 813–825 (1979). Freimark et al. in U.S. Pat. No. 3,755,220 issued Aug. 28, 1973 mention that certain chemical additives known as debonding agents interfere with the natural fiber-to-fiber bonding that occurs during sheet formation in papermaking processes. This reduction in bonding leads to a softer, or less harsh, sheet of paper. Freimark et al. go on to teach the use of wet strength resins to enhance the wet strength of the sheet in conjunction with the use of debonding agents to off-set undesirable effects of the wet strength resin. These debonding agents do reduce dry tensile strength, but there is also generally a reduction in wet tensile strength.

Shaw, in U.S. Pat. No. 3,821,068, issued Jun. 28, 1974, also teaches that chemical debonders can be used to reduce the stiffness, and thus enhance the softness, of a tissue paper web.

Chemical debonding agents have been disclosed in various references such as U.S. Pat. No. 3,554,862, issued to Hervey et al. on Jan. 12, 1971. These materials include quaternary ammonium salts such as trimethylcocoammonium chloride, trimethyloleylammonium chloride, di(hydrogenated) tallow dimethyl ammonium chloride and trimethylstearyl ammonium chloride.

Emanuelsson et al., in U.S. Pat. No. 4,144,122, issued Mar. 13, 1979, teach the use of complex quaternary ammonium compounds such as bis(alkoxy(2-hydroxy)-propylene) quaternary ammonium chlorides to soften webs. These authors also attempt to overcome any decrease in absorbency caused by the debonders through the use of nonionic surfactants such as ethylene oxide and propylene oxide adducts of fatty alcohols.

Armak Company, of Chicago, Ill., in their bulletin 76-17 (1977) disclose that the use of dimethyl di(hydrogenated) tallow ammonium chloride in combination with fatty acid esters of polyoxyethylene glycols may impart both softness and absorbency to tissue paper webs.

One exemplary result of research directed toward improved paper webs is described in U.S. Pat. No. 3,301,746, issued to Sanford and Sisson on Jan. 31, 1967. Despite the high quality of paper webs made by the process described in this patent, and despite the commercial success of products formed from these webs, research efforts directed to finding improved products have continued.

For example, Becker et al. in U.S. Pat. No. 4,158,594, issued Jan. 19, 1979, describe a method they contend will form a strong, soft, fibrous sheet. More specifically, they teach that the strength of a tissue paper web (which may have been softened by the addition of chemical debonding agents) can be enhanced by adhering, during processing, one surface of the web to a creping surface in a fine patterned arrangement by a bonding material (such as an acrylic latex rubber emulsion, a water soluble resin, or an elastomeric bonding material) which has been adhered to one surface of the web and to the creping surface in the fine patterned arrangement, and creping the web from the creping surface to form a sheet material.

Conventional quaternary ammonium compounds such as the well known dialkyl dimethyl ammonium salts (e.g. ditallow dimethyl ammonium chloride, ditallow dimethyl ammonium methyl sulfate, di(hydrogenated) tallow dimethyl ammonium chloride etc . . . ) are effective chemical debonding agents. Unfortunately, these quaternary ammonium compounds are not biodegradable. Applicant has discovered that biodegradable mono- and di-ester variations of these quaternary ammonium salts also function effectively as chemical debonding agents and enhance the softness of fibrous cellulose materials.

It is an object of this invention to provide a biodegradable chemical softening composition useful for treating fibrous cellulose materials It is a further object of this invention to provide soft, absorbent tissue paper products.

It is also a further object of this invention to provide a process for making soft, absorbent tissue paper products.

These and other objects are obtained using the present invention, as will become readily apparent from a reading of the following disclosure.

SUMMARY OF THE INVENTION

The present invention provides a biodegradable chemical softening composition useful for treating fibrous cellulose materials. Briefly, the biodegradable chemical softening composition comprises a mixture of:

(a) a quaternized ester-amine compound having the formula $$\begin{array}{c} R_2 \\ \diagdown \\ N^+ \\ \diagup \diagdown \\ R_2 \quad R_1 \end{array} (CH_2)_2-O-\overset{O}{\underset{\|}{C}}-R_3 \quad X^-$$

or $$\begin{array}{c} R_2 \\ \diagdown \\ N^+ \\ \diagup \diagdown \\ R_2 \quad (CH_2)_2-O-\underset{\|}{C}-R_3 \\ \quad\quad\quad\quad O \end{array} (CH_2)_2-O-\overset{O}{\underset{\|}{C}}-R_3 \quad X^-$$

wherein each $R_2$ substituent is a $C_1$-$C_{66}$ alkyl or hydroxyalkyl group, or mixture thereof; each $R_1$ substituent is a $C_{14}$-$C_{22}$ hydrocarbyl group, or mixture thereof; each $R_3$ subtituent is a $C_{12}$-$C_{20}$ hydrocarbyl group, or mixture thereof; and $X^-$ is a compatible anion; and (b) a polyhydroxy compound selected from the group consisting of glycerol, and polyethylene glycols and polypropylene glycols having a weight average molecular weight from about 200 to 4000;

wherein the weight ratio of the quaternized ester-amine compound to the polyhydroxy compound ranges from about 1:0.1 to 0.1:1; and wherein said polyhydroxy compound is miscible with the quaternized ester-amine compound at a temperature of at least 50° C.

Preferably, the mixture of the quaternized ester-amine and the polyhydroxy compound is diluted with a liquid carrier to a concentration of from about 0.01% to about 25.0% by weight of the chemical softening composition before being added to the fibrous cellulose material. Preferably, the temperature of the liquid carrier ranges from about 40° C. to about 80° C. and the pH is less than about 4. Preferably, at least 20% of the polyhydroxy compound and the quaternized ester-amine compound added to the fibrous cellulose are retained.

Examples of preferred quaternized ester-amine compounds suitable for use in the present invention include compounds having the formulas:

$$(CH_3)_2-N^+-CH_2CH_2-O-\overset{O}{\underset{\|}{C}}-C_{16}H_{33} \quad X^-$$
$$\quad\quad\ \ |$$
$$\quad\quad C_{18}H_{37}$$

and $$(CH_3)_2-N^+-(CH_2CH_2-O-\overset{O}{\underset{\|}{C}}-C_{16}H_{33})_2 \quad X^-$$

These compounds can be considered to be mono and diester variations of the well-known dialkyldimethylammonium salts such as diester ditallow dimethyl ammonium chloride, monoester ditallow dimethyl ammonium chloride, diester di(hydrogenated)tallow dimethyl ammonium methylsulfate, diester di(hydrogenated)tallow dimethyl ammonium chloride, monoester di(hydrogenated)tallow dimethyl ammonium chloride, with the diester variations of di(non hydrogenated)tallow dimethyl ammonium chloride, di(touch hydrogenated)tallow dimethyl ammonium chloride and di(hydrogenated)tallow dimethyl ammonium chloride being preferred. Depending upon the product characteristic requirements, the saturation level of the ditallow can be tailored from non hydrogenated (soft) to touch, partial or complete hydrogenation (hard).

Without being bound by theory, it is believed that the ester moiety(ies) lends biodegradability to these compounds. Importantly, the quaternized ester-amine compounds used herein biodegrade more rapidly than conventional dialkyl dimethyl ammonium chemical softeners.

Examples of polyhydroxy compounds useful in the present invention include glycerol and polyethylene glycols having a weight average molecular weight of from about 200 to about 4000, with polyethylene glycols having a weight average molecular weight of from about 200 to about 600 being preferred.

Briefly, the process for making the tissue webs of the present invention comprises the steps of formation is a papermaking furnish from the aforementioned components, deposition of the papermaking furnish onto a foraminous surface such as a Fourdrinier wire, and removal of the water from the deposited furnish.

All percentages, ratios and proportions herein are by weight unless otherwise specified.

BRIEF DESCRIPTION OF THE DRAWINGS

While the Specification concludes with claims particularly pointing out and and distinctly claiming the present invention. it is believed the invention is better understood from the following description taken in conjunction with the associated drawings, in which:

Figure 1:
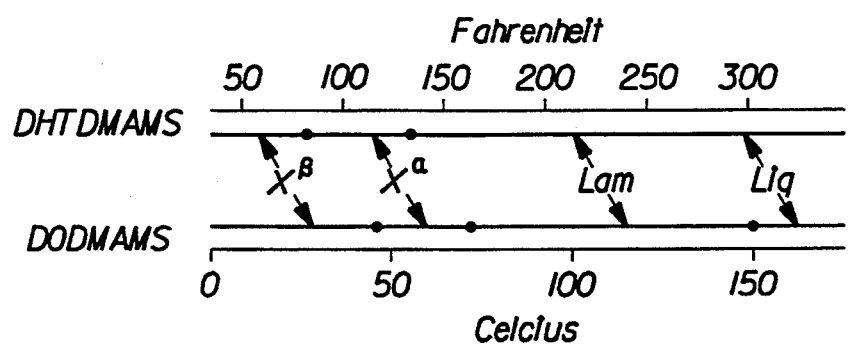
FIG. 1 is a phase diagram of DODMAMS and DHTDMAMS.

The present invention is described in more detail below.

DETAILED DESCRIPTION OF THE INVENTION

While this specification concludes with claims particularly pointing out and distinctly claiming the subject matter regarded as the invention, it is believed that the invention can be better understood from a reading of the following detailed description and of the appended examples.

As used herein, the terms tissue paper web, paper web, web, paper sheet and paper product all refer to sheets of paper made by a process comprising the steps of forming an aqueous papermaking furnish, depositing this furnish on a foraminous surface, such as a Fourdrinier wire, and removing the water from the furnish as by gravity or vacuum-assisted drainage, with or without pressing, and by evaporation.

As used herein, an aqueous papermaking furnish is an aqueous slurry of papermaking fibers and the chemicals described hereinafter.

The first step in the process of this invention is the forming of an aqueous papermaking furnish. The furnish comprises papermaking fibers (hereinafter sometimes referred to as wood pulp), and a mixture of at least one quaternized ester-amine compound and at least one polyhydroxy compound, all of which will be hereinafter described.

It is anticipated that wood pulp in all its varieties will normally comprise the papermaking fibers used in this invention. However, other cellulose fibrous pulps, such as cotton liners, bagasse, rayon, etc., can be used and none are disclaimed. Wood pulps useful herein include chemical pulps such as Kraft, sulfite and sulfate pulps as well as mechanical pulps including for example, ground wood, thermomechanical pulps and chemically modified thermomechanical pulp (CTMP). Pulps derived from both deciduous and coniferous trees can be used. Also applicable to the present invention are fibers derived from recycled paper, which may contain any or all of the above categories as well as other non-fibrous materials such as fillers and adhesives used to facilitate the original papermaking. Preferably, the papermaking fibers used in this invention comprise Kraft pulp derived from northern softwoods.

Biodegradable Chemical Softener Compositions

The present invention contains as an essential component a mixture of a quaternized ester-amine compound and a polyhydroxy compound. The ratio of the quaternized ester-amine compound to the polyhydroxy compound ranges from about 1:0.1 to 0.1:1; preferably, the weight ratio of the quaternized ester-amine compound to the polyhydroxy compound is about 1:0.3 to 0.3:1; more preferably, the weight ratio of the quaternized ester-amine compound to the polyhydroxy compound is about 1:0.7 to 0.7:1 , although this ratio will vary depending upon the molecular weight of the particular polyhdroxy compound and/or quaternized ester-amine compound used.

Each of these types of compounds will be described in detail below.

A. Quaternized Ester-Amine Compound

The chemical softening composition contains as an essential component a quaternized ester-amine compound having the formula:

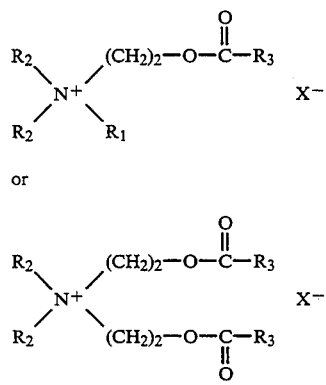

or

In the structures named above each $R_1$ is a $C_{14}$–$C_{22}$ hydrocarbyl group, preferably tallow $C_{16}$–$C_{18}$ alkyl; $R_2$ is a $C_1$–$C_6$ alkyl or hydroxyalkyl group, preferably $C_1$–$C_3$ alkyl; $R_3$ is $C_{12}$–$C_{20}$ hydrocarbyl group, preferably $C_{14}$–$C_{16}$ alkyl, $X^-$ is a compatible anion, such as an halide (e.g. chloride or bromide) or methyl sulfate. As discussed in Swern, Ed. in Bailey's Industrial Oil and Fat Products, Third Edition, John Wiley and Sons (New York 1964), tallow is a naturally occurring material having a variable composition. Table 6.13 in the above-identified reference edited by Swern indicates that typically 78% or more of the fatty acids of tallow contain 16 or 18 carbon atoms. Typically, half of the fatty acids present in tallow are unsaturated, primarily in the form of oleic acid. Synthetic as well as natural "tallows" fall within the scope of the present invention. It is also known that depending upon the product characteristic requirements, the saturation level of the ditallow can be tailored from non hydrogenated (soft) to touch, partial or complete hydrogenation (hard).

It will be understood that substituents $R_1$, $R_2$, $R_3$ may optionally be substituted with various groups such as alkoxyl, hydroxyl, or can be branched, but such materials are not preferred herein. Preferably, each $R_1$ is $C_{16}$–$C_{18}$ alkyl, most preferably each $R_1$ is straight-chain $C_{18}$ alkyl. Preferably, each $R_2$ is methyl. Preferably $R_3$ is $C_{14}$–$C_{16}$ alkyl, most preferably $R_3$ is straight chain $C_{16}$ alkyl and $X^-$ is chloride or methyl sulfate.

Specific examples of quaternized ester-amine compounds having the structures named above and suitable for use in the present invention include the well-known diester dialkyl dimethyl ammonium salts such as diester ditallow dimethyl ammonium chloride, monoester ditallow dimethyl ammonium chloride, diester ditallow dimethyl ammonium methyl sulfate, diester di(hydrogenated)tallow dimethyl ammonium methyl sulfate, diester di(hydrogenated)tallow dimethyl ammonium chloride. Diester ditallow dimethyl ammonium chloride and diester di(hydrogenated)tallow dimethyl ammonium chloride are particularly preferred. These particular materials are available commercially from Sherex Chemical Company Inc. of Dublin, Ohio under the tradename "ADOGEN DDMC®".

Di-quat variations of the quaternized ester-amine compound can also be used, and are meant to fall within the scope of the present invention. These compounds have the formula:

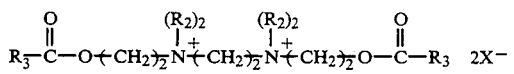

In the structure named above each $R_2$ is a $C_1$-$C_6$ alkyl or hydroalkyl group, $R_3$ is $C_{12}$-$C_{20}$ hydrocarbyl group, $X^-$ is a compatible anion, such as an halide (e.g., chloride or bromide) or methyl sulfate. Preferably, each $R_3$ is $C_{14}$-$C_{16}$ alkyl, most preferably each $R_3$ is straight-chain $C_{16}$ alkyl, and $R_2$ is a methyl.

B. Polyhydroxy Compound

The chemical softening composition contains as an essential component a polyhydroxy compound.

Examples of polyhydroxy compounds useful in the present invention include glycerol, and polyethylene glycols and polypropylene glycols having a weight average molecular weight of from about 200 to about 4000, preferably from about 200 to about 1000, most preferably from about 200 to about 600. Polyethylene glycols having an weight average molecular weight of from about 200 to about 600 are especially preferred.

A particularly preferred polyhydroxy compound is polyethylene glycol having an weight average molecular weight of about 400. This material is available commercially from the Union Carbide Company of Danbury, Conn. under the tradename "PEG-400".

The chemical softening composition described above i.e. mixture of a quaternized ester-amine compounds and a polyhydroxy compound are preferably added to the aqueous slurry of papermaking fibers, or furnish, in the wet end of the papermaking machine at some suitable point ahead of the Fourdrinier wire or sheet forming stage. However, applications of the above described chemical chemical softening composition subsequent to formation of a wet tissue web and prior to drying of the web to completion will also provide significant softness, absorbency, and wet strength benefits and are expressly included within the scope of the present invention.

Figure 6:
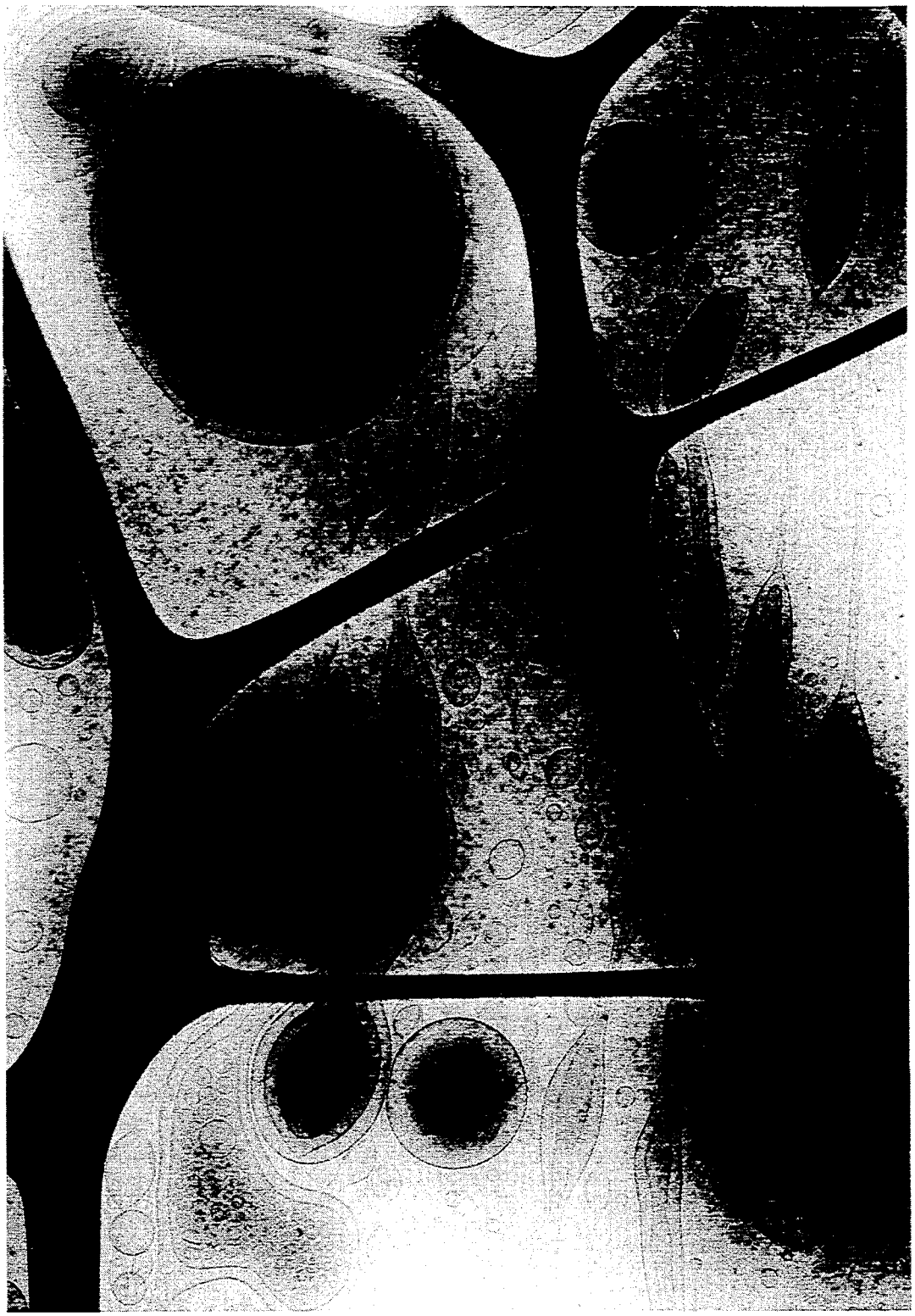
FIG. 6 is a cryo-transmission micro-photograph taken at X 63,000 of the vesicle dispersion of a 1:1 by weight ratio of a diester ditallow dimethyl ammonium chloride and PEG-400 system.
Figure 7:
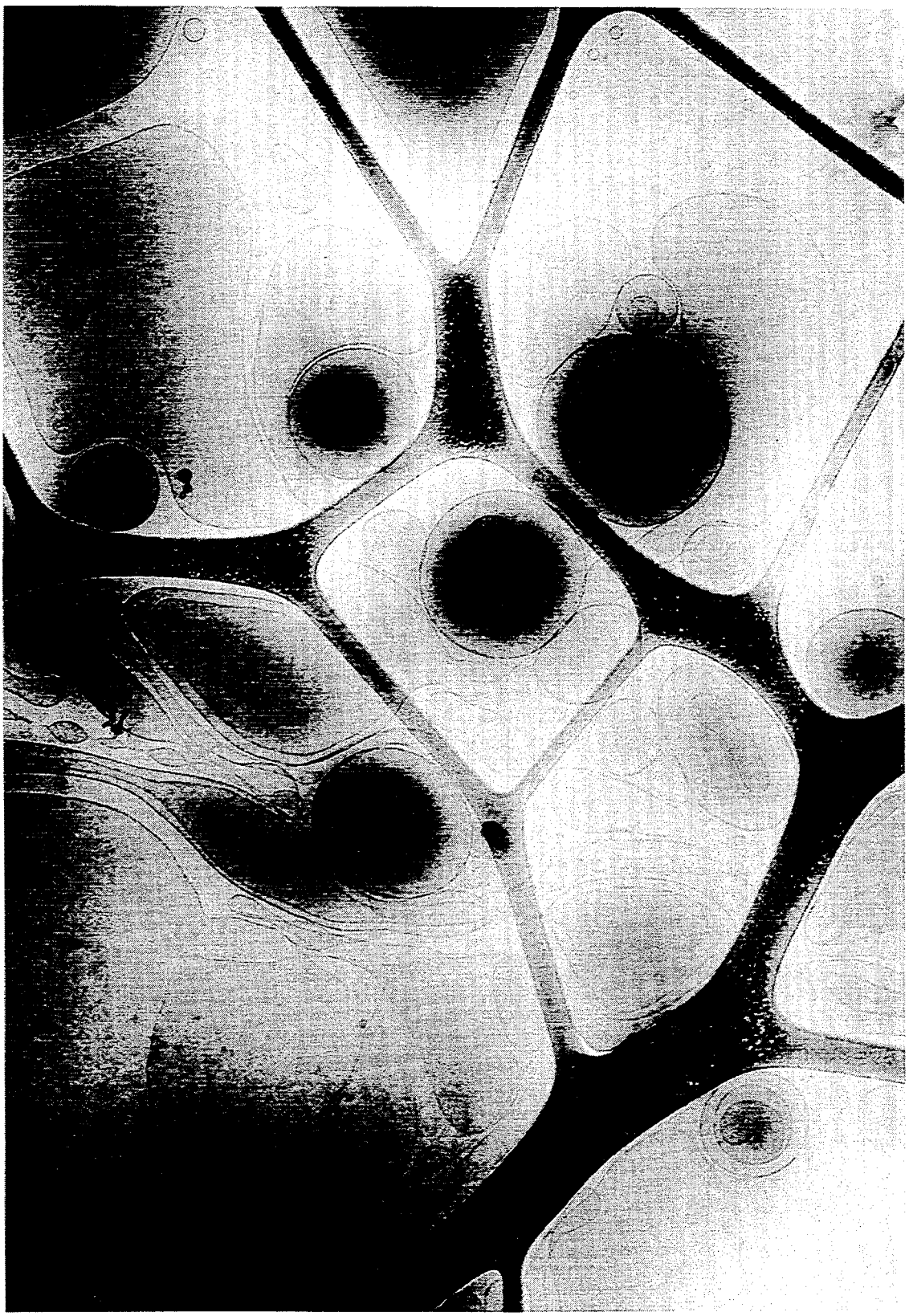
FIG. 7 is a cryo-transmission micro-photograph taken at X 63,000 of the vesicle dispersion of a 1:1 by weight ratio of a diester ditallow dimethyl ammonium chloride and glycerol system.
Figure 8:
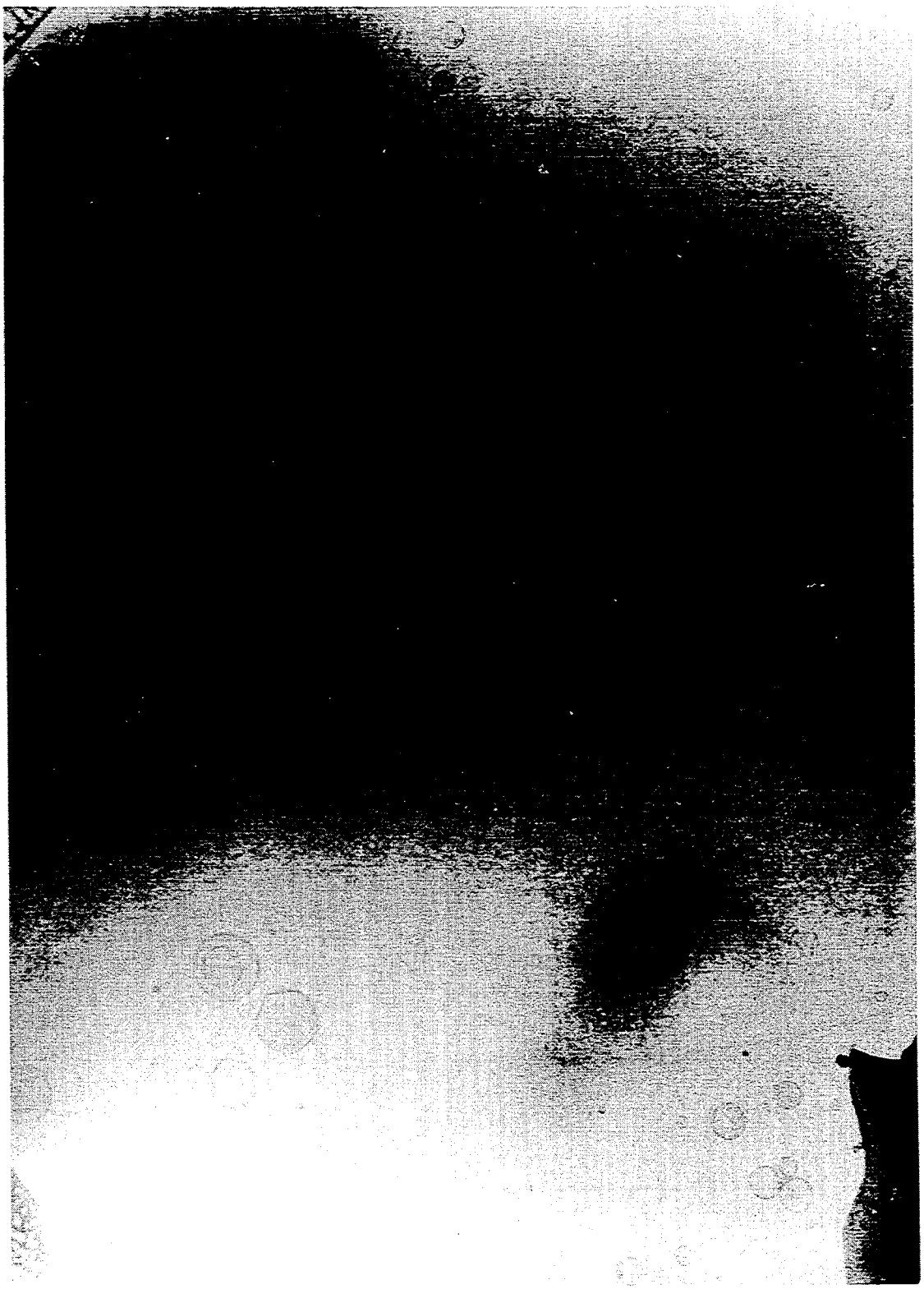
FIG. 8 is a cryo-transmission micro-photograph taken at X 66,000 of the vesicle dispersion of a 1:1 by weight ratio of a diester di(hydrogenated) tallow dimethyl ammonium chloride and PEG-400 system.

It has been discovered that the chemical softening composition is more effective when the quaternized ester-amine compound and the polyhydroxy compound are first pre-mixed together before being added to the papermaking furnish. A preferred method, as will be described in greater detail hereinafter in Example 1, consists of first heating the polyhydroxy compound to a temperature of about 66° C. (150° F.), and then adding the quaternized ester-amine compound to the hot polyhydroxy compound to form a fluidized "melt". The weight ratio of the quaternized ester-amine compound to the polyhydroxy compound ranges from about 1:0.1 to 0.1:1; preferably, the weight ratio of the quaternized ester-amine compound to the compound is about 1:0.3 to 0.3:1; more preferably, the weight ratio of the quaternized ester-amine compound to the compound is about 1:0.7 to 0.7:1, although this ratio will vary depending upon the molecular weight of the particular compound and/or quaternized ester-amine compound used. The quaternized ester-amine compound and polyhydroxy compound melt is then diluted to the desired concentration, and mixed to form an aqueous solution containing a vesicle dispersion of the quaternized ester-amine compound/polyhydroxy compound mixture which is then added to the papermaking furnish. Preferably, the mixture of the quaternized ester-amine compound and polyhdroxy compound is diluted with a liquid carrier such as water to a concentration of from about 0.01% to about 25% by weight of the softening composition before being added to the papermaking furnish. The pH of the liquid carrier preferably ranges from 2 to 4. The temperature of the liquid carrier preferably ranges from about 40° C. to about 80° C. The mixture of the quaternized ester-amine compound and the polyhydroxy compound are present as particles dispersed in the liquid carrier. The average particle size preferably ranges from about 0.01 to 10 microns, most preferably from about 0.1 to about 1.0 micron. As shown in FIGS. 6–8, the dispersed particles are in the form of vesicle particles.

The quaternized ester-amine compound and the polyhdroxy compound are mixed at an elevated temperature of at least 50° C., more preferably from about 50° C. to about 100° C. Without wishing to be bound by theory, it is believed at the preferred temperature range, that both Diester Ditallow Dimethyl Ammonium Chloride (DEDTDMAC) and Diester Di(hydrogenated)tallow Dimethyl Ammonium Chloride (DEDHTDMAC) are in a liquid phase and are miscible with the polyhdroxy compound. The physical states of Di(hydrogenated) tallow Dimethyl Ammonium Methyl sulfate (DHTDMAMS) will be discussed in greater detail hereinafter.

The papermaking furnish can be readily formed or prepared by mixing techniques and equipment well known to those skilled in the papermaking art.

It has unexpectedly been found that the adsorption of the polyhydroxy compound onto paper is significantly enhanced when it is premixed with the quaternized ester-amine compound before being added to the paper. In fact, at least 20% of the polyhydroxy compound and the quaternized ester-amine compound added to the fibrous cellulose are retained; and preferably, the retention level of quaternized ester-amine compound and the polyhydroxy compound is from about 50% to about 90% by weight of the dry fibers.

Importantly, adsorption occurs at a concentration and within a time frame that are practical for use during paper making. In an effort to better understand the surprisingly high retention rate of polyhydroxy compound onto the paper, the physical science of the melted solution and the aqueous dispersion of a di(hydrogenated) tallow dimethyl ammonium methyl sulfate and polyethylene glycol 400 were studied.

Without wishing to be bound by theory, or to otherwise limit the present invention, the following discussion is offered for explaining how the quaternary ammonium compound promotes the adsorption of the polyhydroxy compound onto paper.

Information on the physical state of DHTDMAMS Di(hydrogenated)Tallow dimethyl Ammonium Methyl Sulfate, $(C_{17}H_{35})_2N^+(CH_3)_2,CH_3OSO_3^-$); DODMAMS (Dioctadecyl Dimethyl Ammonium Methyl Sulfate, $(C_{18}H_{37})_2N^+(CH_3)_2,CH_3OSO_3^-$); DEDTDMAC ((Diester Ditallow Dimethyl Ammonium Chloride, $(CH_3)_2N^+(CH_2CH_2OCOC_{16}H_{33})_2,Cl^-$) and DEDHTDMAC (Diester Di(hydrogenated) Tallow Dimethyl Ammonium Chloride) is provided by X-ray and NMR data on the commercial mixture. DODMAMS is a major component of DHTDMAMS, and serves as a model compound for the commercial mixture. It is useful to consider first the simpler DODMAMS system, and then the more complex commercial DHTDMAMS mixture.

Depending on the temperature, DODMAMS may exist in any of four phase states (FIG. 1): two polymorphic crystals ($X^\beta$ and $X^\alpha$), a lamellar (Lam) liquid-crystal, or a liquid phase. The $X^\beta$ crystal exists from below room temperature to 47° C. At this temperature it is transformed into the polymorphic $X^\alpha$ crystal, which at 72° C. is transformed into the Lam liquid crystal phase. This phase, in turn, is transformed into an isotropic liquid at 150° C. A lamellar (Lam) liquid-crystal phase does also exist in both DEDTDMAC and DEDHTDMAC compounds. DHTDMAMS is expected to resemble DODMAMS in its physical behavior, except that the temperatures of the phase transitions will be lowered and broadened. For example, the transition from the $X^\beta$ to the $X^\alpha$ crystal occurs at 27° C. in DHTDMAMS instead of 47° C. as in DODMAMS. Also, calorimetric data indicate that several crystal→Lam phase transitions occur in DHTDMAMS rather than one as in DODMAMS. The onset temperature of the highest of these transitions is 56° C., in good agreement with the X-ray data, but calorimetry displays two peaks with onset temperatures of 59° and 63° C.

DODMAC (Dioctadecyl Dimethyl Ammonium Chloride) displays qualitatively different behavior from DODMAMS and in that the Lam liquid crystal phase does not exist in this compound. This difference, however, is believed not to be important to the use of this compound (or its commercial analog DHTDMAC) in the treatment of paper. (Laughlin et al., Journal of Physical Chemistry, Physical Science of the Dioctadecyldimethylammonium Chloride-Water System. 1. Equilibrium Phase Behavior, 1990, volume 94, pages 2546-2552, incorporated herein by reference.

Mixtures of DHTDMAMS with PEG 400

Figure 2:
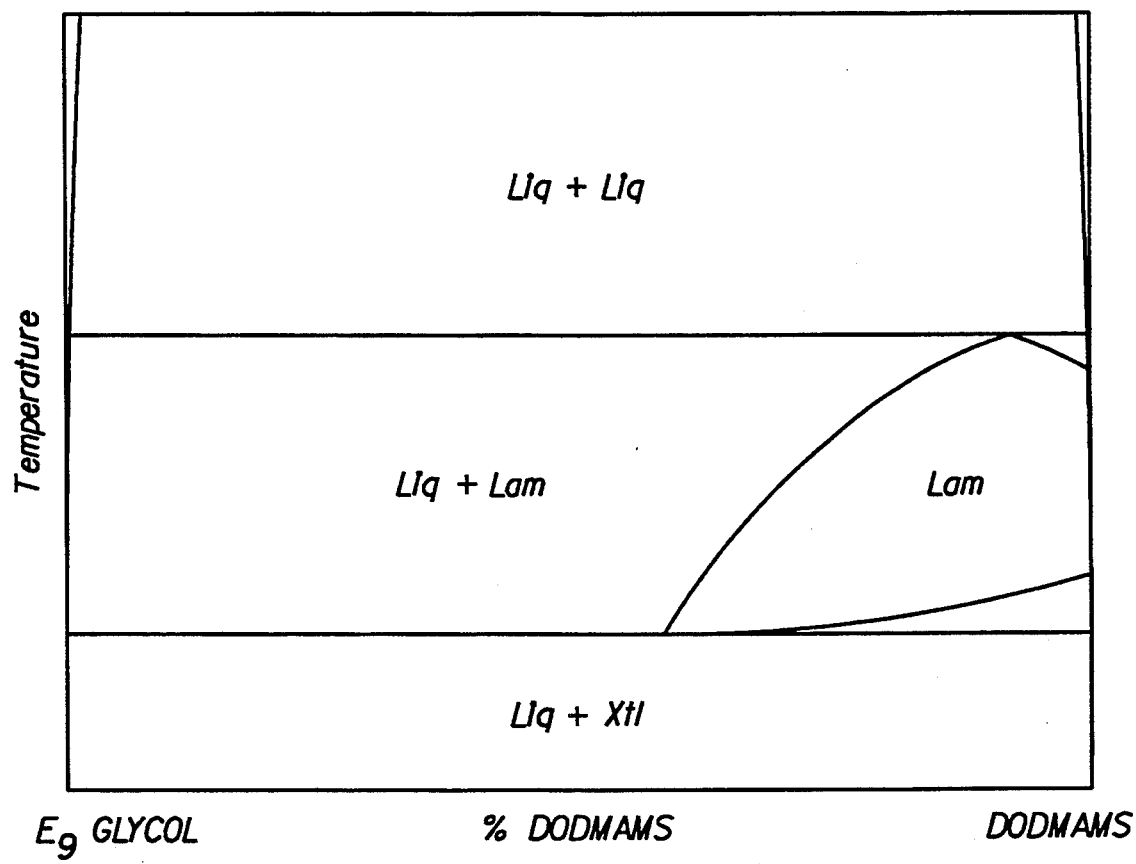
FIG. 2 is a phase diagram of DODMAMS and PEG-400 system.
Figure 3:
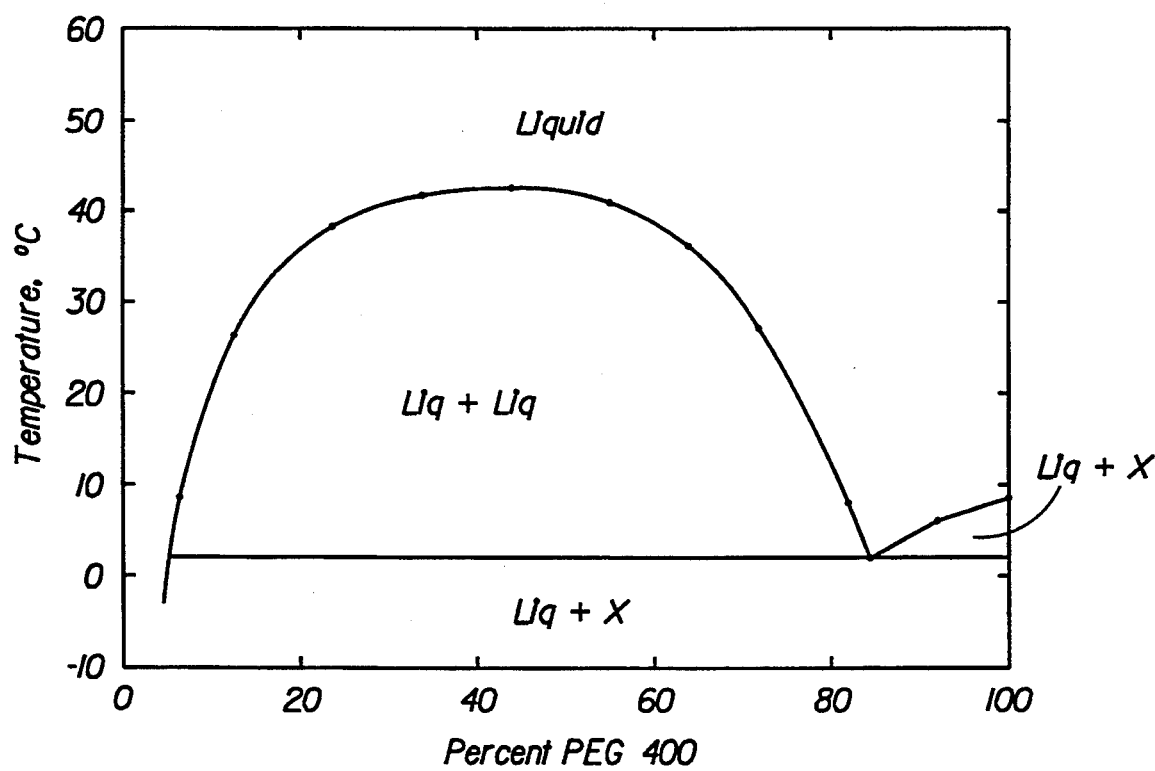
FIG. 3 is a phase diagram of PEG-400/methyl octanoate system.

A 1:1 weight ratio mixture of these two materials is studied, and a plausible model for the phase behavior of this system is suggested in FIG. 2. In this diagram DODMAMS and PEG are shown to be immiscible at high temperatures, where they coexist as two liquid phases. As mixtures of the two liquids within this region are cooled, a Lam phase separates from the mixture. This study therefore shows that these two materials while immiscible at high temperatures do become miscible at lower temperatures within the Lam liquid crystal phase. At still lower temperatures crystal phases are expected to separate from the Lam phase, and the compounds are again immiscible.

These studies therefore suggest that in order to form good dispersions of DHTDMAMS and PEG-400 in water, the premix that is diluted with water should be held within the intermediate temperature range where the two compounds are miscible.

Mixtures of DHTDMAC with PEG 400

Phase studies of these two materials using the step-wise dilution method demonstrate that their physical behavior is considerably different from that of DHTDMAMS. No liquid crystal phases are found. These compounds are miscible over a wide range of temperatures, which indicates that dispersions may be prepared from these mixtures over a comparable range of temperatures. No upper temperature limit of miscibility exists.

Mixtures of DEDTDMAC with PEG 400

Figure 4:
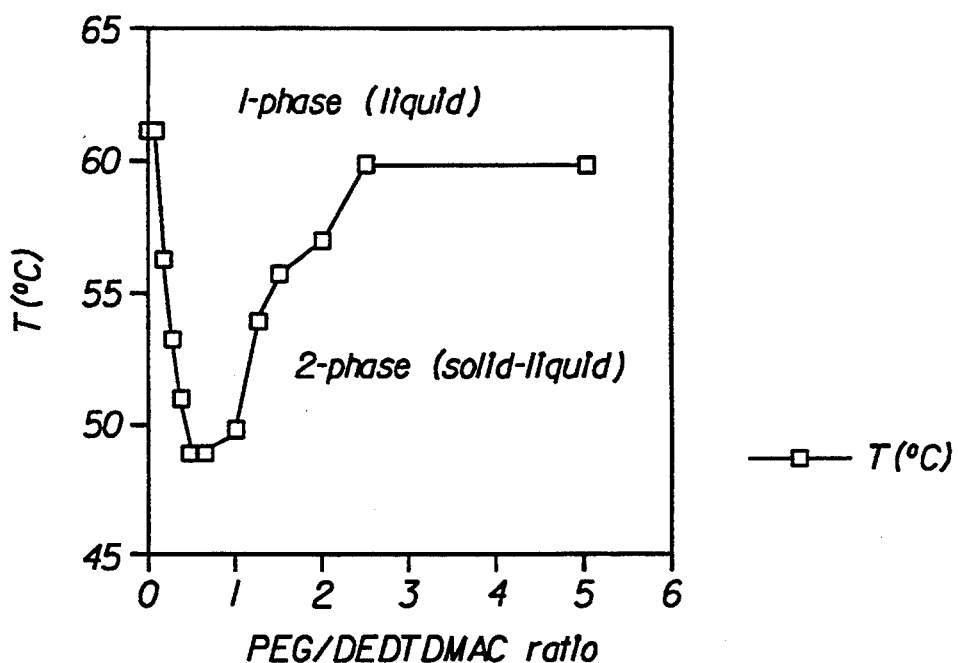
FIG. 4 is a phase diagram of DEDTDMAC and PEG-400 system.

Phase studies (FIG. 4) of these two materials using the step-wise dilution method demonstrate that their physical behavior is similar from that of DHTDMAC. These compounds are miscible over a wide range of temperatures (>50° C.), which indicates that dispersions may be prepared from these mixtures over a comparable range of temperatures. No upper temperature limit of miscibility exists.

Mixtures of DEDHTDMAC with PEG 400

Figure 5:
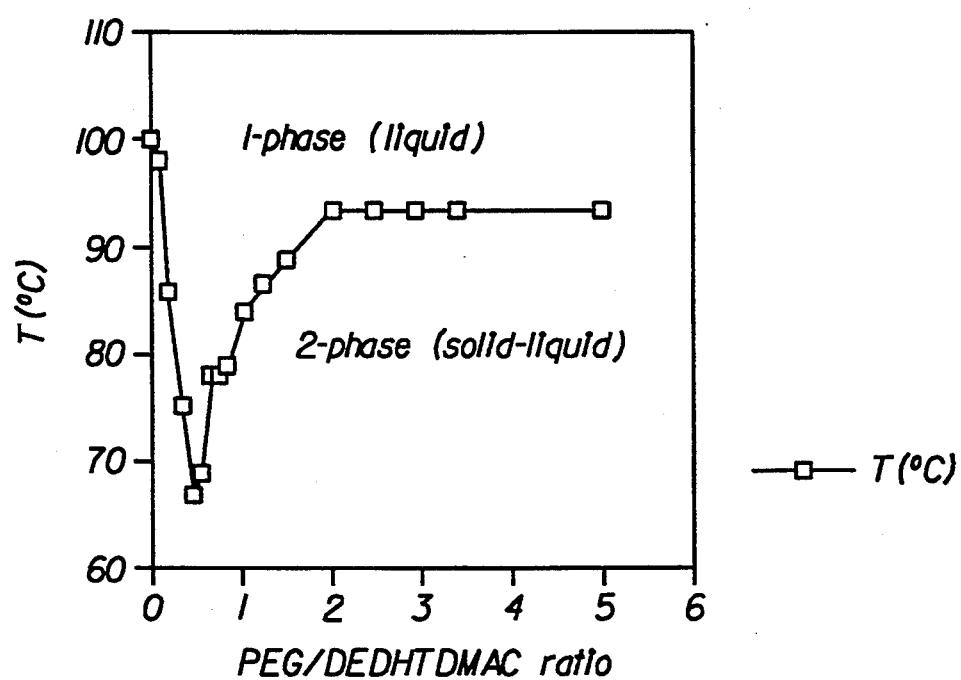
FIG. 5 is a phase diagram of DEDHTDMAC and PEG-400 system.

Phase studies (FIG. 5) of these two materials using the step-wise dilution method demonstrate that their physical behavior is similar from that of DHTDMAC. These compounds are miscible over a wide range of temperatures (>67° C.), which indicates that dispersions may be prepared from these mixtures over a comparable range of temperatures. No upper temperature limit of miscibility exists.

Preparation of Dispersions

Dispersions of either of these materials may be prepared by diluting a mixture, that is held at a temperature at which the polyhydroxy compound and the quaternary ammonium salt are miscible, with water. It does not matter greatly whether they are miscible within a liquid crystalline phase (as in the case of DHTDMAMS), or in a liquid phase (as in the case of DHTDMAC). Neither DHTDMAMS nor DHTDMAC are soluble in water, so the dilution of either dry phase with water will precipitate the quaternary ammonium compound as small particles. Both quaternary ammonium compounds will precipitate at elevated temperatures as a liquid-crystal phase in dilute aqueous solutions, regardless of whether the dry solution was liquid or liquid crystalline. The polyhydroxy compound is soluble with water in all proportions, so it is not precipitated.

Cryoelectron microscopy demonstrates that the particles present are about 0.1 to 1.0 micrometers in size, and highly varied in structure. Some are sheets (curved or flat), while others are closed vesicles. The membranes of all these particles are bilayers of molecular dimensions in which the head groups are exposed to water, the tails are together. The PEG is presumed to be associated with these particles. The application of dispersions prepared in this manner to paper results in attachment of the quaternary ammonium ion to the paper, strongly promotes the adsorption of the polyhydroxy compound onto paper, and produces the desired modification of softness and retention of wettability.

State of the Dispersions

When the above described dispersions are cooled, the partial crystallization of the material within the colloidal particles may occur. However, it is likely that the attainment of the equilibrium state will require a long time (perhaps months), so that a disordered particle whose membranes are either a liquid crystal or a disordered crystal phase is interacting with the paper. Preferably, the chemical softening compositions described herein are used before the equilibrium state has been attained.

It is believed that the vesicles containing DHTDMAMS and PEG break apart upon drying of the fibrous cellulosic material. Once the vesicle is broken, the majority of the PEG component penetrates into the interior of the cellulose fibers where it enhances the fiber flexibility. Importantly, some of the PEG is retained on the surface of the fiber where it acts to enhance the absorbency rate of the cellulose fibers. Due to ionic interaction, the cationic portion of the DHTDMAMS component stays on the surface of the cellulose fiber where it enhances the surface feel and softness of the paper product.

The second step in the process of this invention is the depositing of the papermaking furnish using the above described chemical softener composition as an additive on a foraminous surface and the third step is the removing of the water from the furnish so deposited. Techniques and equipment which can be used to accomplish these two processing steps will be readily apparent to those skilled in the papermaking art. Prefered tissue paper embodiments of the present invention contain from about 0.005% to about 5.0%, more preferably from about 0.03% to 0.5% by weight, on a dry fiber basis of the chemical softening composition described herein.

The present invention is applicable to tissue paper in general, including but not limited to conventionally felt-pressed tissue paper; pattern densified tissue paper such as exemplified in the aforementioned U.S. Patent by Sanford-Sisson and its progeny; and high bulk, uncompacted tissue paper such as exemplified by U.S. Pat. No. 3,81 2,000, Salvucci, Jr., issued May 21, 1974. The tissue paper may be of a homogenous or multilayered construction; and tissue paper products made therefrom may be of a single-ply or multi-ply construction. Tissue structures formed from layered paper webs are described in U.S. Pat. No. 3,994,771, Morgan, Jr. et al. issued Nov. 30, 1976, and incorporated herein by reference. In general, a wet-laid composite, soft, bulky and absorbent paper structure is prepared from two or more layers of furnish which are preferably comprised of different fiber types. The layers are preferably formed from the deposition of separate streams of dilute fiber slurries, the fibers typically being relatively long softwood and relatively short hardwood fibers as used in tissue papermaking, upon one or more endless foraminous screens. The layers are subsequently combined to form a layered composite web. The layer web is subsequently caused to conform to the surface of an open mesh drying/imprinting fabric by the application of a fluid to force to the web and thereafter thermally predried on said fabric as part of a low density papermaking process. The layered web may be stratified with respect to fiber type or the fiber content of the respective layers may be essentially the same. The tissue paper preferably has a basis weight of between 10 g/m$^2$ and about 65 g/m$^2$, and density of about 0.60 g/cc or less. Preferably, basis weight will be below about 35 g/m$^2$ or less; and density will be about 0.30 g/cc or less. Most preferably, density will be between 0.04 g/cc and about 0.20 g/cc.

Conventionally pressed tissue paper and methods for making such paper are known in the art. Such paper is typically made by depositing papermaking furnish on a foraminous forming wire. This forming wire is often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided in a pressurized headbox. The headbox has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls.

The dewatered web is then further pressed and dried by a stream drum apparatus known in the art as a Yankee dryer. Pressure can be developed at the Yankee dryer by mechanical means such as an opposing cylindrical drum pressing against the web. Vacuum may also be applied to the web as it is pressed against the Yankee surface. Multiple Yankee dryer drums may be employed, whereby additional pressing is optionally incurred between the drums. The tissue paper structures which are formed are referred to hereinafter as conventional, pressed, tissue paper structures. Such sheets are considered to be compacted since the web is subjected to substantial overall mechanical compressional forces while the fibers are moist and are then dried (and optionally creped) while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones may be discretely spaced within the high bulk field or may be interconnected, either fully or partially, within the high bulk field. Preferred processes for making pattern densified tissue webs are disclosed in U.S. Pat. No. 3,301,746, issued to Sanford and Sisson on Jan. 31, 1967, U.S. Pat. No. 3,974,025, issued to Peter G. Ayers on Aug. 10, 1976, and U.S. Pat. No. 4,191,609, issued to Paul D. Trokhan on Mar. 4, 1980, and U.S. Pat. No. 4,637,859, issued to Paul D. Trokhan on Jan. 20, 1987; all of which are incorporated herein by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further dedensified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones may be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned displacement of knuckles which operate as the array of supports which facilitate the formation of the densified zones upon application of pressure. The pattern of knuckles constitutes the array of supports previously referred to. Imprinting carrier fabrics are disclosed in U.S. Pat. No. 3,301,746, Sanford and Sisson, issued Jan. 31, 1967, U.S. Pat. No. 3,821,068, Salvucci, Jr. et al., issued May 21, 1974, U.S. Pat. No. 3,974,025, Ayers, issued Aug. 10, 1976, U.S. Pat. No. 3,573,164, Friedberg et al., issued Mar. 30, 1971, U.S. Pat. No. 3,473,576, Amneus, issued Oct. 21, 1969, U.S. Pat. No. 4,239,065, Trokhan, issued Dec. 16, 1980, and U.S. Pat. No. 4,528,239, Trokhan, issued Jul. 9, 1985, all of which are incorporated herein by reference.

Preferably, the furnish is first formed into a wet web on a foraminous forming carrier, such as a Fourdrinier wire. The web is dewatered and transferred to an imprinting fabric. The furnish may alternately be initially deposited on a foraminous supporting carrier which also operates as an imprinting fabric. Once formed, the wet web is dewatered and, preferably, thermally pre-dried to a selected fiber consistency of between about 40% and about 80%. Dewatering can be performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll which supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure may be applied to induce impression of densified zones during initial dewatering, in a separate, subsequent process stage, or a combination thereof.

Uncompacted, nonpattern-densified tissue paper structures are described in U.S. Pat. No. 3,812,000 issued to Joseph L. Salvucci, Jr. and Peter N. Yiannos on May 21,1974 and U.S. Pat. No. 4,208,459, issued to Henry E. Becker, Albert L. McConnell, and Richard Schutte on Jun. 17, 1980, both of which are incorporated herein by reference. In general, uncompacted, non pattern densified tissue paper structures are prepared by depositing a papermaking furnish on a foraminous forming wire such as a Fourdrinier wire to form a wet web, draining the web and removing additional water without mechanical compression until the web has a fiber consistency of at least 80%, and creping the web. Water is removed from the web by vacuum dewatering and thermal drying. The resulting structure is a soft but weak high bulk sheet of relatively uncompacted fibers. Bonding material is preferably applied to portions of the web prior to creping.

Compacted non-pattern-densified tissue structures are commonly known in the art as conventional tissue structures. In general, compacted, non-patterndensified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25-50%, transferring the web to a thermal dryer such as a Yankee and creping the web. Overall, water is removed from the web by vacuum, mechanical pressing and thermal means. The resulting structure is strong and generally of singular density, but very low in bulk, absorbency and in softness.

The tissue paper web of this invention can be used in any application where soft, absorbent tissue paper webs are required. Particularly advantageous uses of the tissue paper web of this invention are in paper towel, toilet tissue and facial tissue products. For example, two tissue paper webs of this invention can be embossed and adhesively secured together in face to face relation as taught by U.S. Pat. No. 3,414,459, which issued to Wells on Dec. 3, 1968 and which is incorporated herein by reference, to form 2-ply paper towels.

Molecular Weight Determination

A. Introduction

The essential distinguishing characteristic of polymeric materials is their molecular size. The properties which have enabled polymers to be used in a diversity of applications derive almost entirely from their macromolecular nature. In order to characterize fully these materials it is essential to have some means of defining and determining their molecular weights and molecular weight distributions. It is more correct to use the term relative molecular mass rather the molecular weight, but the latter is used more generally in polymer technology. It is not always practical to determine molecular weight distributions. However, this is becoming more common practice using chromatographic techniques. Rather, recourse is made to expressing molecular size in terms of molecular weight averages.

B. Molecular weight averages

If we consider a simple molecular weight distribution which represents the weight fraction ($w_i$) of molecules having relative molecular mass ($M_i$), it is possible to define several useful average values. Averaging carried out on the basis of the number of molecules ($N_i$) of a particular size ($M_i$) gives the Number Average Molecular Weight $$\overline{M}_n = \frac{\Sigma N_i M_i}{\Sigma N_i}$$

An important consequence of this definition is that the Number Average Molecular Weight in grams contains Avogadro's Number of molecules. This definition of molecular weight is consistent with that of monodisperse molecular species, i.e. molecules having the same molecular weight. Of more significance is the recognition that if the number of molecules in a given mass of a polydisperse polymer can be determined in some way then $\overline{M}_n$, can be calculated readily. This is the basis of colligative property measurements.

Averaging on the basis of the weight fractions ($W_i$) of molecules of a given mass ($M_i$) leads to the definition of Weight Average Molecular Weights $$\overline{M}_w = \frac{\Sigma W_i N_i}{\Sigma W_i} = \frac{\Sigma N_i M_i^2}{\Sigma N_i M_i}$$

$\overline{M}_w$ is a more useful means for expressing polymer molecular weights than $\overline{M}_n$ since it reflects more accurately such properties as melt viscosity and mechanical properties of polymers and is therefor used in the present invention.

Analytical and Testing Procedures

Analysis of the amount of biodegradable treatment chemicals used herein or retained on tissue paper webs can be performed by any method accepted in the applicable art.

A. Quantitative analysis for quaternized ester-amine and polyhydroxy compounds

For example, the level of the quaternized ester-amine compound, such as diester di(hydrogenated)tallow dimethyl ammonium chloride (DEDHTDMAC) (i.e., ADOGEN DDMC ®), retained by the tissue paper can be determined by solvent extraction of the DEDHTDMAC by an organic solvent followed by an anionic/cationic titration using Dimidium Bromide as indicator; the level of the polyhydroxy compound, such as PEG-400, can be determined by extraction in an aqueous solvent such as water followed by gas chromatography or colorimetry techniques to determine the level of PEG-400 in the extract. These methods are exemplary, and are not meant to exclude other methods which may be useful for determining levels of particular components retained by the tissue paper.

B. Hydrophilicity (absorbency)

Hydrophilicity of tissue paper refers, in general, to the propensity of the tissue paper to be wetted with water. Hydrophilicity of tissue paper may be somewhat quantified by determining the period of time required for dry tissue paper to become completely wetted with water. This period of time is referred to as "wetting time". In order to provide a consistent and repeatable test for wetting time, the following procedure may be used for wetting time determinations:first, a conditioned sample unit sheet (the environmental conditions for testing of paper samples are $23°+1°$ C. and $50+2\%$ R.H. as specified in TAPPI Method T 402), approximately $4\frac{3}{8}$ inch $\times 4\frac{3}{4}$ inch (about 11.1 cm $\times$ 12 cm) of tissue paper structure is provided; second, the sheet is folded into four (4) juxtaposed quarters, and then crumpled into a ball approximately 0.75 inches (about 1.9 cm) to about 1 inch (about 2.5 cm) in diameter; third, the balled sheet is placed on the surface of a body of distilled water at $23°\pm1°$ C. and a timer is simultaneously started; fourth, the timer is stopped and read when wetting of the balled sheet is completed. Complete wetting is observed visually.

Hydrophilicity characters of tissue paper embodiments of the present invention may, of course, be determined immediately after manufacture. However, substantial increases in hydrophobicity may occur during the first two weeks after the tissue paper is made:i.e., after the paper has aged two (2) weeks following its manufacture. Thus, the wetting times are preferably measured at the end of such two week period. Accordingly, wetting times measured at the end of a two week aging period at room temperature are referred to as "two week wetting times."

C. Density

The density of tissue paper, as that term is used herein, is the average density calculated as the basis weight of that paper divided by the caliper, with the appropriate unit conversions incorporated therein. Caliper of the tissue paper, as used herein, is the thickness of the paper when subjected to a compressive load of $g/in^2$ ( 15.5 $g/cm^2$).

Optional Ingredients

Other chemicals commonly used in papermaking can be added to the biodegradable chemical softening composition described herein, or to the papermaking furnish so long as they do not significantly and adversely affect the softening, absorbency of the fibrous material, and enhancing actions of the chemical softening composition.

For example, surfactants may be used to treat the tissue paper webs of the present invention. The level of surfactant, if used, is preferably from about 0.01% to about 2.0% by weight, based on the dry fiber weight of the tissue paper. The surfactants preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as Crodesta SL-40 which is available from Croda, Inc. (New York, N.Y.); alkylglycoside ethers as described in U.S. Pat. No. 4,011,389, issued to W. K. Langdon, et al. on Mar. 8, 1977; and alkylpolyethoxylated esters such as pegosperse 200 ML available from Glyco Chemicals, Inc. (Greenwich, Conn.) and IGEPAL RC-520 available from Rhone Poulenc Corporation (Cranbury, N.J.).

Other types of chemicals which may be added, include dry strength additives to increase the tensile strength of the tissue webs. Examples of dry strength additives include carboxymethyl cellulose, and cationic polymers from the ACCO chemical family such as ACCO 711 and ACCO 51 4, with ACCO chemical family being preferred. These materials are available commercially from the American Cyanamid Company of Wayne, N.J. The level of dry strength additive, if used, is preferably from about 0.01% to about 1.0%, by weight, based on the dry fiber weight of the tissue paper.

Other types of chemicals which may be added, include wet strength additives to increase the wet burst of the tissue webs. The present invention may contain as an optional component from about 0.01% to about 3.0%, more preferably from about 0.3% to about 1.5% by weight, on a dry fiber weight basis, of a water-soluble permanent wet strength resin.

Permanent wet strength resins useful herein can be of several types. Generally, those resins which have previously found and which will hereafter find utility in the papermaking art are useful herein. Numerous examples are shown in the aforementioned paper by Westfelt, incorporated herein by reference.

In the usual case, the wet strength resins are water-soluble, cationic materials. That is to say, the resins are water-soluble at the time they are added to the papermaking furnish. It is quite possible, and even to be expected, that subsequent events such as cross-linking will render the resins insoluble in water. Further, some resins are soluble only under specific conditions, such as over a limited pH range.

Wet strength resins are generally believed to undergo a cross-linking or other curing reactions after they have been deposited on, within, or among the papermaking fibers. Cross-linking or curing does not normally occur so long as substantial amounts of water are present.

Of particular utility are the various polyamide-epichlorohydrin resins. These materials are low molecular weight polymers provided with reactive functional groups such as amino, epoxy, and azetidinium groups. The patent literature is replete with descriptions of processes for making such materials. U.S. Pat. No. 3,700,623, issued to Keim on Oct. 24, 1972 and U.S. Pat. No. 3,772,076, issued to Keim on Nov. 13, 1973 are examples of such patents and both are incorporated herein by reference.

Polyamide-epichlorohydrin resins sold under the trademarks Kymene 557H and Kymene 2064 by Hercules Incorporated of Wilmington, Del., are particularly useful in this invention. These resins are generally described in the aforementioned patents to Keim.

Base-activated polyamide-epichlorohydrin resins useful in the present invention are sold under the Santo Res trademark, such as Santo Res 31, by Monsanto Company of St. Louis, Mo. These types of materials are generally described in U.S. Pat. Nos. 3,855,158 issued to Petrovich on Dec. 17, 1974; 3,899,388 issued to Petrovich on Aug. 12, 1975; 4,129,528 issued to Petrovich on Dec. 12, 1978; 4,147,586 issued to Petrovich on Apr. 3, 1979; and U.S. Pat. No. 4,222,921 issued to Van Eenam on Sep. 16, 1980, all incorporated herein by reference.

Other water-soluble cationic resins useful herein are the polyacrylamide resins such as those sold under the Parez trademark, such as Parez 631NC, by American Cyanamid Company of Stanford, Conn. These materials are generally described in U.S. Pat. Nos. 3,556,932 issued to Coscia et al. on Jan. 19, 1971; and 3,556,933 issued to Williams et al. on Jan. 19, 1971, all incorporated herein by reference.

Other types of water-soluble resins useful in the present invention include acrylic emulsions and anionic styrene-butadiene latexes. Numerous examples of these types of resins are provided in U.S. Pat. No. 3,844,880, Meisel, Jr. et al., issued Oct. 29, 1974, incorporated herein by reference.

Still other water-soluble cationic resins finding utility in this invention are the urea formaldehyde and melamine formaldehyde resins. These polyfunctional, reactive polymers have molecular weights on the order of a few thousand. The more common functional groups include nitrogen containing groups such as amino groups and methylol groups attached to nitrogen.

Although less preferred, polyethylenimine type resins find utility in the present invention.

More complete descriptions of the aforementioned water-soluble resins, including their manufacture, can be found in TAPPI Monograph Series No. 29, Wet Strength In Paper and Paperboard, Technical Association of the Pulp and Paper Industry (New York; 1965), incorporated herein by reference. As used herein, the term "permanent wet strength resin" refers to a resin which allows the paper sheet, when placed in an aqueous medium, to keep a majority of its initial wet strength for a period of time greater than at least two minutes.

The above-mentioned wet strength additives typically result in paper products with permanent wet strength, i.e., paper which when placed in an aqueous medium retains a substantial portion of its initial wet strength over time. However, permanent wet strength in some types of paper products can be an unnecessary and undesirable property. Paper products such as toilet tissues, etc., are generally disposed of after brief periods of use into septic systems and the like. Clogging of these systems can result if the paper product permanently retains its hydrolysis-resistant strength properties. More recently, manufacturers have added temporary wet strength additives to paper products for which wet strength is sufficient for the intended use, but which then decays upon soaking in water. Decay of the wet strength facilitates flow of the paper product through septic systems.

Examples of suitable temporary wet strength resins include modified starch temporary wet strength agents, such as National Starch 78-0080, marketed by the National Starch and Chemical Corporation (New York, N.Y.). This type of wet strength agent can be made by reacting dimethoxyethyI-N-methyl-chloroacetamide with cationic starch polymers. Modified starch temporary wet strength agents are also described in U.S. Pat. No. 4,675,394, Solarek, et al., issued Jun. 23, 1987, and incorporated herein by reference. Preferred temporary wet strength resins include those described in U.S. Pat. No. 4,981,557, Bjorkquist, issued Jan. 1, 1991, and incorporated herein by reference.

With respect to the classes and specific examples of both permanent and temporary wet strength resins listed above, it should be understood that the resins listed are exemplary in nature and are not meant to limit the scope of this invention.

Mixtures of compatible wet strength resins can also be used in the practice of this invention.

The above listings of optional chemical additives is intended to be merely exemplary in nature, and are not meant to limit the scope of the invention.

The following examples illustrate the practice of the present invention but are not intended to be limiting thereof.

EXAMPLE 1

The purpose of this example is to illustrate a method that can be used to make-up a biodegradable chemical softener composition comprising a mixture of Diester Ditallow Dimethyl Ammonium Chloride (DEDTDMAC) and Polyethylene Glycol 400 (PEG-400).

A 1% solution of the biodegradable chemical softener is prepared according to the following procedure: 1. An equivalent weight of DEDTDMAC and PEG-400 is weighed separately; 2. PEG is heated up to about 66° C. (150° F.); 3. DEDTDMAC is dissolved in PEG to form a melted solution at 66° C. (150° F.); 4. Shear stress is applied to form a homogeneous mixture of DEDTDMAC in PEG; 5. The pH of the dilution water is adjusted to about 3 by adding a solution of HCl at 0.1% concentration. 6. The dilution water is heated up to about 66° C. (150° F.); 7. The melted mixture of DEDTDMAC and PEG is diluted to a 1% solution; and 8. Shear stress is applied to form an aqueous solution containing a vesicle dispersion or suspension of the DEDTDMAC and PEG mixture; 9. The particle size of the vesicle dispersion is determined using an optical microscopic technique. The particle size range is from about 0.1 to 1.0 micron.

FIG. 6 illustrates a cryo-transmission micro-photograph taken at X 63,000 of a vesicle dispersion of a 1:1 by weight ratio of a DEDTDMAC and PEG-400 system. From FIG. 6, it indicates that particles having membranes one or two bilayers thick, whose geometry ranges from closed/open vesicles, to disc-like structures and sheets.

EXAMPLE 2

The purpose of this example is to illustrate a method that can be used to make-up a biodegradable chemical softener composition which comprises a mixture of Diester Ditallow Dimethyl Ammonium Chloride (DEDTDMAC) and Glycerol.

A 1% solution of the biodegradable chemical softener is prepared according to the following procedure: 1. An equivalent weight of DEDTDMAC and Glycerol is separately weighed; 2. Glycerol is heated up to about 66° C. (150° F.); 3. DEDTDMAC is dissolved in Glycerol to form a melted solution at 66° C. (150° F.); 4. Shear stress is applied to form a homogeneous mixture of DEDTDMAC in Glycerol; 5. The pH of the dilution water is adjusted to about 3 by adding a solution of HCl at 0.1% concentration. 6. The dilution water is heated up to about 66° C. (150° F.); 7. The melted mixture is diluted to a 1% solution; and 8. Shear stress is applied to form an aqueous solution containing a vesicle dispersion or suspension of DEDTDMAC and Glycerol mixture; 9. The particle size of the vesicle dispersion is determined using an optical microscopic technique. The particle size range is from about 0.1 to 1.0 micron.

FIG. 7 illustrates a cryo-transmission micro-photograph taken at X 63,000 of a vesicle dispersion of a 1:1 by weight ratio of a DEDTDMAC and Glycerol system. From FIG. 7, it indicates that particles having membranes one or two bilayers thick, whose geometry ranges from closed vesicles, to disc-like structures.

EXAMPLE 3

The purpose of this example is to illustrate a method that can be used to make-up a biodegradable chemical softener composition comprising a mixture of Diester Di(hydrogenated) Tallow Dimethyl Ammonium Chloride (DEDHTDMAC) (i.e., ADOGEN DDMC R from Sherex company) and Polyethylene glycol 400 (PEG-400).

A 1% solution of the biodegradable chemical softener is prepared according to the following procedure: 1. An equivalent weight of DEDHTDMAC and PEG-400 is separately weighed; 2. PEG is heated up to about 90° C. (194° F.); 3. DEDHTDMAC is dissolved in PEG to form a melted solution at 90° C. (194° F.); 4. Shear stress is applied to form a homogeneous mixture of DEDHTDMAC in PEG; 5. The pH of the dilution water is adjusted to about 3 by adding a solution of HCl at 0.1% concentration. 6. The dilution water is heated up to about 70° C. (158° F.); 7. The melted mixture is diluted to a 1% solution; and 8. Shear stress is applied to form an aqueous solution containing a vesicle dispersion or suspension of DEDHTDMAC and PEG mixture; 9. The particle size of DEDHTDMAC and PEG vesicle dispersion is determined using an optical microscopic technique. The particle size range is from about 0.1 to 1.0 micron.

FIG. 8 illustrates a cryo-transmission micro-photograph taken at X 66,000 of a vesicle dispersion of a 1:1 by weight ratio of a DEDHTDMAC and PEG-400 system. From FIG. 8, it indicates that particles having membranes one or two bilayers thick, whose geometry ranges from closed vesicles, to disc-like structures.

EXAMPLE 4

The purpose of this example is to illustrate a method using a blow through drying papermaking technique to make soft and absorbent paper towel sheets treated with a biodegradable chemical softener composition comprising a mixture of Diester Ditallow Dimethyl Ammonium Chloride (DEDTDMAC), a Polyethylene glycol 400 (PEG-400), and a permanent wet strength resin.

A pilot scale Fourdrinier papermaking machine is used in the practice of the present invention. First, a 1% solution of the biodegradable chemical softener is prepared according to the procedure in Example 1. Second, a 3% by weight aqueous slurry of NSK is made up in a conventional re-pulper. The NSK slurry is refined gently and a 2% solution of a permanent wet strength resin (i.e. Kymene 557H marketed by Hercules incorporated of Wilmington, DE) is added to the NSK stock pipe at a rate of 1% by weight of the dry fibers. The adsorption of Kymene 557H to NSK is enhanced by an in-line mixer. A 1% solution of Carboxy Methyl Cellulose (CMC) is added after the in-line mixer at a rate of 0.2% by weight of the dry fibers to enhance the dry strength of the fibrous substrate. The adsorption of CMC to NSK can be enhanced by an in-line mixer. Then, a 1% solution of the chemical softener mixture (DEDTDMAC/PEG) is added to the NSK slurry at a rate of 0.1% by weight of the dry fibers. The adsorption of the chemical softener mixture to NSK can also enhanced via an in-line mixer. The NSK slurry is diluted to 0.2% by the fan pump. Third, a 3% by weight aqueous slurry of CTMP is made up in a conventional re-pulper. A non-ionic surfactant (Pegosperse) is added to the re-pulper at a rate of 0.2% by weight of dry fibers. A 1% solution of the chemical softener mixture is added to the CTMP stock pipe before the stock pump at a rate of 0.1% by weight of the dry fibers. The adsorption of the chemical softener mixture to CTMP can be enhanced by an in-line mixer. The CTMP slurry is diluted to 0.2% by the fan pump. The treated furnish mixture (NSK / CTMP) is blended in the head box and deposited onto a Foudrinier wire to form an embryonic web. Dewatering occurs through the Foudrinier wire and is assisted by a deflector and vacuum boxes. The Fourdrinier wire is of a 5-shed, satin weave configuration having 84 machine-direction and 76 cross-machine-direction monofilaments per inch, respectively. The embryonic wet web is transferred from the Fourdrinier wire, at a fiber consistency of about 22% at the point of transfer, to a photo-polymer fabric having 240 Linear Idaho cells per square inch, 34 percent knuckle areas and 14 mils of photo-polymer depth. Further de-watering is accomplished by vacuum assisted drainage until the web has a fiber consistency of about 28%. The patterned web is pre-dried by air blow-through to a fiber consistency of about 65% by weight. The web is then adhered to the surface of a Yankee dryer with a sprayed creping adhesive comprising 0.25% aqueous solution of Polyvinyl Alcohol (PVA). The fiber consistency is increased to an estimated 96% before the dry creping the web with a doctor blade. The doctor blade has a bevel angle of about 25 degrees and is positioned with respect to the Yankee dryer to provide an impact angle of about 81 degrees; the Yankee dryer is operated at about 800 fpm (feet per minute) (about 244 meters per minute). The dry web is formed into roll at a speed of 700 fpm (214 meters per minutes).

Two plies of the web are formed into paper towel products by embossing and laminating them together using PVA adhesive. The paper towel has about 26 #/3M Sq Ft basis weight, contains about 0.2% of the biodegradable chemical softener mixture and about 1.0% of the permanent wet strength resin. The resulting paper towel is soft, absorbent, and very strong when wetted.

Table 1 below summarizes the retention levels and the average particle size of the DEDTDMAC/PEG- 400 vesicle dispersion compared to adding PEG-400 only to the furnish slurry.

TABLE 1

| | PEG to slurry | DEDTDMAC/PEG vesicle dispersion |
|---|---|---|
| Retention level of PEG in product (%) | 5 | 80 |
| Retention level of DEDTDMAC in product (%) | NA | 85 |
| Average particle size (microns) | NA | 0.4 |

EXAMPLE 5

The purpose of this example is to illustrate a method using a blow through drying and layered papermaking techniques to make soft and absorbent toilet tissue paper treated with a biodegradable chemical softener composition comprising a mixture of Diester Ditallow Dimethyl Ammonium Methyl Chloride (DEDTDMAC) and a Polyethylene glycol 400 (PEG-400) and a temporary wet strength resin.

A pilot scale Fourdrinier papermaking machine is used in the practice of the present invention. First, a 1% solution of the biodegradable chemical softener is prepared according to the procedure in Example 1. Second, a 3% by weight aqueous slurry of NSK is made up in a conventional re-pulper. The NSK slurry is refined gently and a 2% solution of the temporary wet strength resin (i.e. National starch 78-0080 marketed by National Starch and Chemical corporation of New York, N.Y.) is added to the NSK stock pipe at a rate of 0.75% by weight of the dry fibers. The adsorption of the temporary wet strength resin onto NSK fibers is enhanced by an in-line mixer. The NSK slurry is diluted to about 0.2% consistency at the fan pump. Third, a 3% by weight aqueous slurry of Eucalyptus fibers is made up in a conventional re-pulper. A 1% solution of the chemical softener mixture is added to the Eucalyptus stock pipe before the stock pump at a rate of 0.2% by weight of the dry fibers. The adsorption of the biodegradable chemical softener mixture to Eucalyptus fibers can be enhanced by an in-line mixer. The Eucalyptus slurry is diluted to about 0.2% consistency at the fan pump.

The treated furnish mixture (30% of NSK / 70% of Eucalyptus) is blended in the head box and deposited onto a Foudrinier wire to form an embryonic web. Dewatering occurs through the Foudrinier wire and is assisted by a deflector and vacuum boxes. The Fourdrinier wire is of a 5-shed, satin weave configuration having 84 machine-direction and 76 cross-machine-direction monofilaments per inch, respectively. The embryonic wet web is transferred from the photo-polymer wire, at a fiber consistency of about 15% at the point of transfer, to a photo-polymer fabric having 562 Linear Idaho cells per square inch, 40 percent knuckle area and 9 mils of photo-polymer depth. Further de-watering is accomplished by vacuum assisted drainage until the web has a fiber consistency of about 28%. The patterned web is pre-dried by air blow-through to a fiber consistency of about 65% by weight. The web is then adhered to the surface of a Yankee dryer with a sprayed creping adhesive comprising 0.25% aqueous solution of Polyvinyl Alcohol (PVA). The fiber consistency is increased to an estimated 96% before the dry creping the web with a doctor blade. The doctor blade has a bevel angle of about 25 degrees and is positioned with respect to the Yankee dryer to provide an impact angle of about 81 degrees; the Yankee dryer is operated at about 800 fpm (feet per minute) (about 244 meters per minute). The dry web is formed into roll at a speed of 700 fpm (214 meters per minutes).

The web is converted into a one ply tissue paper product. The tissue paper has about 18#/3M Sq R basis weight, contains about 0.1% of the biodegradable chemical softener mixture and about 0.2% of the temporary wet strength resin. Importantly, the resulting tissue paper is soft, absorbent and is suitable for use as facial and/or toilet tissues.

Table 2 below summarizes the retention levels and the average particle size of the DEDTDMAC / PEG vesicle dispersion compared to adding PEG-400 only to the furnish slurry.

TABLE 2

| | PEG to slurry | DEDTDMAC/PEG Vesicle dispersion |
|---|---|---|
| Retention level of PEG in product (%) | 5 | 75 |
| Retention level of DEDTDMAC in product (%) | NA | 85 |
| Average particle size (microns) | NA | 0.4 |

EXAMPLE 6

The purpose of this example is to illustrate a method using a blow through drying papermaking technique to make soft and absorbent toilet tissue paper treated with a biodegradable chemical softener composition comprising a mixture of Diester Ditallow Dimethyl Ammonium Chloride (DEDTDMAC), a Polyethylene glycol 400 (PEG-400) and a dry strength additive resin.

A pilot scale Fourdrinier papermaking machine is used in the practice of the present invention. First, a 1% solution of the biodegradable chemical softener is prepared according to the procedure in Example 1. Second, a 3% by weight aqueous slurry of NSK is made up in a conventional re-pulper. The NSK slurry is refined gently and a 2% solution of the dry strength resin (i.e. Acco 514, Acco 711 marketed by American Cyanamid company of Fairfield, OH) is added to the NSK stock pipe at a rate of 0.2% by weight of the dry fibers. The adsorption of the dry strength resin onto NSK fibers is enhanced by an in-line mixer. The NSK slurry is diluted to about 0.2% consistency at the fan pump. Third, a 3% by weight aqueous slurry of Eucalyptus fibers is made up in a conventional re-pulper. A 1% solution of the chemical softener mixture is added to the Eucalyptus stock pipe before the stock pump at a rate of 0.2% by weight of the dry fibers. The adsorption of the biodegradable chemical softener mixture to Eucalyptus fibers can be enhanced by an in-line mixer. The Eucalyptus slurry is diluted to about 0.2% consistency at the fan pump.

The treated furnish mixture (30% of NSK / 70% of Eucalyptus) is blended in the head box and deposited onto a Foudrinier wire to form an embryonic web. Dewatering occurs through the Foudrinier wire and is assisted by a deflector and vacuum boxes. The Fourdrinier wire is of a 5-shed, satin weave configuration having 84 machine-direction and 76 cross-machine-direction monofilaments per inch, respectively. The embryonic wet web is transferred from the photo-polymer wire, at a fiber consistency of about 15% at the point of transfer, to a photo-polymer fabric having 562 Linear Idaho cells per square inch, 40 percent knuckle area and 9 mils of photo-polymer depth. Further de-watering is accomplished by vacuum assisted drainage until the web has a fiber consistency of about 28%. The patterned web is pre-dried by air blow-through to a fiber consistency of about 65% by weight. The web is then adhered to the surface of a Yankee dryer with a sprayed creping adhesive comprising 0.25% aqueous solution of Polyvinyl Alcohol (PVA). The fiber consistency is increased to an estimated 96% before the dry creping the web with a doctor blade. The doctor blade has a bevel angle of about 25 degrees and is positioned with respect to the Yankee dryer to provide an impact angle of about 81 degrees; the Yankee dryer is operated at about 800 fpm (feet per minute) (about 244 meters per minute). The dry web is formed into roll at a speed of 700 fpm ( 21 4 meters per minutes).

Two plies of the web are formed into tissue paper products and laminating them together using ply bonded technique. The tissue paper has about 23#/3M Sq Ft basis weight, contains about 0.1% of the biodegradable chemical softener mixture and about 0.1% of the dry strength resin. Importantly, the resulting tissue paper is soft, absorbent and is suitable for use as facial and/or toilet tissues.

Table 3 below summarizes the retention levels and the average particle size of the DEDTDMAC / PEG-400 vesicle dispersion compared to adding PEG-400 only to the furnish slurry.

TABLE 3

|  | PEG to slurry | DEDTDMAC/PEG Vesicle dispersion |
|---|---|---|
| Retention level of PEG in product (%) | 5 | 75 |
| Retention level of DEDTDMAC in product (%) | NA | 80 |
| Average particle size (microns) | NA | 0.4 |

EXAMPLE 7

The purpose of this example is to illustrate a method using a conventional drying papermaking technique to make soft and absorbent toilet tissue paper treated with a biodegradable chemical softener composition comprising a mixture of Diester Di(hydrogenated) Tallow Dimethyl Ammonium Chloride (DEDHTDMAC), a Polyethylene glycol 400 (PEG-400) and a dry strength additive resin.

A pilot scale Fourdrinier papermaking machine is used in the practice of the present invention. First, a 1% solution of the biodegradable chemical softener is prepared according to the procedure in example 3. Second, a 3% by weight aqueous slurry of NSK is made up in a conventional re-pulper. The NSK slurry is refined gently and a 2% solution of the dry strength resin (i.e. Acco 51 4, Acco 711 marketed by American Cyanamid company of Wayne, New Jersey) is added to the NSK stock pipe at a rate of 0.2% by weight of the dry fibers. The adsorption of the dry strength resin onto NSK fibers is enhanced by an in-line mixer. The NSK slurry is diluted to about 0.2% consistency at the fan pump. Third, a 3% by weight aqueous slurry of Eucalyptus fibers is made up in a conventional re-pulper. A 1% solution of the chemical softener mixture is added to the Eucalyptus stock pipe before the stock pump at a rate of 0.2% by weight of the dry fibers. The adsorption of the chemical softener mixture to Eucalyptus fibers can be enhanced by an in-line mixer. The Eucalyptus slurry is diluted to about 0.2% consistency at the fan pump.

The treated furnish mixture (30% of NSK / 70% of Eucalyptus) is blended in the head box and deposited onto a Foudrinier wire to form an embryonic web. Dewatering occurs through the Foudrinier wire and is assisted by a deflector and vacuum boxes. The Foudrinier wire is of a 5-shed, satin weave configuration having 84 machine-direction and 76 cross-machine-direction monofilaments per inch, respectively. The embryonic wet web is transferred from the Foudrinier wire, at a fiber consistency of about 15% at the point of transfer, to a conventional felt. Further de-watering is accomplished by vacuum assisted drainage until the web has a fiber consistency of about 35%. The web is then adhered to the surface of a Yankee dryer. The fiber consistency is increased to an estimated 96% before the dry creping the web with a doctor blade. The doctor blade has a bevel angle of about 25 degrees and is positioned with respect to the Yankee dryer to provide an impact angle of about 81 degrees; the Yankee dryer is operated at about 800 fpm (feet per minute) (about 244 meters per minute). The dry web is formed into roll at a speed of 700 fpm (214 meters per minutes).

Two plies of the web are formed into tissue paper products and laminating them together using ply bonded technique. The tissue paper has about 23#/3M Sq Ft basis weight, contains about 0.1% of the biodegradable chemical softener mixture and about 0.1% of the dry strength resin. Importantly, the resulting tissue paper is soft, absorbent and is suitable for use as a facial and/or toilet tissues.

Table 4 below summarizes the retention levels and the average particle size of the DEDHTDMAC and PEG-400 vesicle dispersion compared to adding PEG-00 only to the furnish slurry.

TABLE 4

|  | PEG to slurry | DEDHTDMAC/PEG Vesicle dispersion |
|---|---|---|
| Retention level of PEG in product (%) | 5 | 70 |
| Retention level of DEDHTDMAC in product (%) | NA | 75 |
| Average particle size (microns) | NA | 0.5 |

What is claimed is:

1. A biodegradable chemical paper softening composition consisting essentially of a mixture of:

(a) a quaternized ester-amine compound having the formula

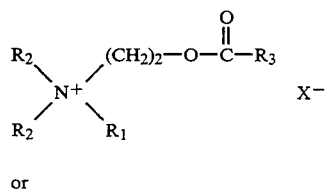

or

-continued

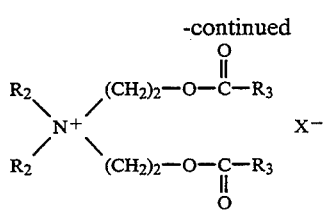

wherein each $R_2$ substituent is a $C_1$–$C_6$ alkyl or hydroxyalkyl group, or mixture thereof; each $R_1$ substituent is a $C_{14}$–$C_{22}$ hydrocarbyl group, or mixture thereof; each $R_3$ substituent is a $C_{12}$–$C_{20}$ hydrocarbyl group, or mixture thereof; and $X^-$ is a compatible anion; and (b) a polyhydroxy compound selected from the group consisting of polyethylene glycols and polypropylene glycols having a weight average molecular weight from about 200 to 4000, wherein the weight ratio of the quaternized ester-amine compound to the polyhydroxy compound ranges from about 1:0.1 to 0.1:1, wherein said polyhydroxy compound is mixed with said quaternized ester-amine compound at a temperature wherein said quaternized esteramine compound and said polyhydroxy compound are miscible.

2. The biodegradable chemical softening composition of claim 1 wherein each $R_2$ is selected from $C_1$–$C_3$ alkyl, each $R_1$ is selected from $C_{16}$–$C_{18}$ alkyl and each $R_3$ is selected from C14–$C_{16}$ alkyl.

3. The biodegradable chemical softening composition of claim 2 wherein each $R_2$ is methyl.

4. The biodegradable chemical softening composition of claim 1 wherein $X^-$ is chloride or methyl sulfate.

5. The biodegradable chemical softening composition of claim 4 wherein the quaternized ester-amine compound is diester di(non hydrogenated) tallow dimethyl ammonium chloride.

6. The biodegradable chemical softening composition of claim 4 wherein the quaternized ester-amine compound is diester di(touch hydrogenated) tallow dimethyl ammonium chloride.

7. The biodegradable chemical softening composition of claim 4 wherein the quaternized ester-amine compound is diester di(partially hydrogenated) tallow dimethyl ammonium chloride.

8. The biodegradable chemical softening composition of claim 4 wherein the quaternized ester-amine compound is diester di(hydrogenated) tallow dimethyl ammonium chloride.

9. The biodegradable chemical softening composition of claim 4 wherein the quaternized ester-amine compound is diester ditallow dimethyl ammonium methyl sulfate.

10. The biodegradable chemical softening composition of claim 4 wherein the quaternized ester-amine compound is diester di(hydrogenated) tallow dimethyl ammonium methyl sulfate.

11. The biodegradable chemical softening composition of claim 5 wherein the polyhydroxy compound is miscible with the diester di(non hydrogenated)tallow dimethyl ammonium chloride in the liquid phase.

12. The biodegradable chemical softening composition of claim 6 wherein the polyhydroxy compound is miscible with the diester di(touch hydrogenated)tallow dimethyl ammonium chloride in the liquid phase.

13. The biodegradable chemical softening composition of claim 7 wherein the polyhydroxy compound is miscible with the diester di(partially hydrogenated)tallow dimethyl ammonium chloride in the liquid phase.

14. The biodegradable chemical softening composition of claim 8 wherein the polyhydroxy compound is miscible with the diester di(hydrogenated) tallow dimethyl ammonium chloride in the liquid phase.

15. The biodegradable chemical softening composition of claim 1 wherein said polyhydroxy compound is a polyethylene glycol having a weight average molecular weight from about 200 to about 1000.

16. The biodegradable chemical softening composition of claim 1 wherein said polyhydroxy compound is a polypropylene glycol having a weight average molecular weight from about 200 to about 1000.

17. The biodegradable chemical softening composition of claim 1 wherein the weight ratio of the quaternized ester-amine compound to the polyhydroxy compound ranges from about 1:0.3 to 0.3:1.

18. The biodegradable chemical softening composition of claim 17 wherein the weight ratio of the quaternized ester-amine compound to the polyhydroxy compound ranges from about 1:0.7 to 0.7:1.

19. The biodegradable chemical softening composition of claim 1 wherein the quaternized ester-amine compound is mixed with the polyhydroxy compound at a temperature of at least 50° C.

20. The biodegradable chemical softening composition of claim 19 wherein the quaternized ester-amine compound is mixed with the polyhydroxy compound at a temperature ranging from about 50° C. to 100° C.

21. The biodegradable chemical softening composition of claim 1 wherein the mixture of the quaternized ester-amine compound and the polyhydroxy compound is diluted with an aqueous carrier to a concentration of from about 0.01% to about 25.0% by weight of the chemical softening composition.

22. The biodegradable chemical softening composition of claim 21 wherein the mixture of the quaternized ester-amine compound and the polyhydroxy compound is present as particles dispersed in the aqueous carrier.

23. The biodegradable chemical softening composition of claim 21 wherein the temperature of the aqueous carrier ranges from about 40° C. to 80° C.

24. The biodegradable chemical softening composition of claim 21 wherein the pH of the aqueous carrier is less than about 4.

25. The biodegradable chemical softening composition of claim 22 wherein the average particle size of the quaternized ester-amine compound and the polyhydroxy compound ranges from about 0.01 to 10 microns.

26. The biodegradable chemical softening composition of claim 25 wherein the average particle size of the quaternized ester-amine compound and the polyhydroxy compound ranges from about 0.1 to 1.0 micron.

27. The biodegradable chemical softening composition of claim 15 wherein the polyhydroxy compound is polyethylene glycol having a molecular weight of from about 200 to about 600.

28. The biodegradable chemical softening composition of claim 16 wherein the polyhydroxy compound is polypropylene glycol having a molecular weight of from about 200 to about 600.

29. The biodegradable chemical softening composition of claim 27 wherein the weight ratio of the quaternized ester-amine compound to the polyhydroxy compound ranges from about 1:0.7 to 0.7:1.

30. The biodegradable chemical softening composition of claim 28 wherein the weight ratio of the quaternized ester-amine compound to the polyhydroxy compound ranges from about 1:0.7 to 0.7:1.

31. The biodegradable chemical softening composition of claim 22 wherein the dispersed particles are vesicle particles.

32. The biodegradable chemical softening composition of claim 1 wherein said quaternized ester-amine compound is in a liquid state when mixed with said polyhdroxy compound.

* * * * *